United States Patent
Ebel et al.

(12)

(10) Patent No.: US 6,303,836 B1
(45) Date of Patent: Oct. 16, 2001

(54) METHOD FOR PRODUCING 2-CYCLODODECYL-1-PROPANOL

(75) Inventors: Klaus Ebel, Lampertheim; Rolf Pinkos, Bad Dürkheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/424,258

(22) PCT Filed: Jun. 4, 1998

(86) PCT No.: PCT/EP98/03339

§ 371 Date: Dec. 1, 1999

§ 102(e) Date: Dec. 1, 1999

(87) PCT Pub. No.: WO98/57914

PCT Pub. Date: Dec. 23, 1998

(30) Foreign Application Priority Data

Jun. 17, 1997 (DE) ............................................. 197 25 533

(51) Int. Cl.$^7$ .................................................. C07C 35/20
(52) U.S. Cl. ........................... 568/821; 568/835; 568/375
(58) Field of Search ..................................... 568/821, 835, 568/375

(56) References Cited

U.S. PATENT DOCUMENTS 4,393,245 * 7/1983 Hoffman et al. ...................... 568/375
4,948,780 * 8/1990 Hafner et al. ............................ 512/8

OTHER PUBLICATIONS

Hans–Henning Vogel, Synthesis, No. 3, pp. 99–140, 1970.*

* cited by examiner

*Primary Examiner*—Samuel Barts
*Assistant Examiner*—Elvis O. Price
(74) *Attorney, Agent, or Firm*—Oblon, Spivak, McClelland, Maier & Neustadt, P.C.

(57) ABSTRACT

2-Cyclododecyl-propanol [sic], which is in demand as musk scent, is prepared in an advantageous industrial process by reacting cyclododecene with an excess of propionic acid or of a propionic acid derivative in the presence of catalytic amounts of a free-radical initiator, and subsequently catalytically hydrogenating the 2-cyclododecylpropionic acid which is formed or the corresponding 2-cyclododecylpropionic acid derivatives.

7 Claims, No Drawings

METHOD FOR PRODUCING 2-CYCLODODECYL-1-PROPANOL

This is the U.S. national stage application of PCT/EP98/03339 filed Jun. 4, 1998.

The present application relates to an advantageous industrial process for preparing 2-cyclododecyl-1-propanol from cyclododecene and propionic acid or derivatives thereof.

2-Cyclododecyl-1-propanol (also called hydroxyambrane) is a scent of the musk class and is becoming increasingly important (cf. EP 278 384 B1). The current process for preparing it starts from cyclododecanone and alkyl 2-bromopropionates (cf., for example, Angew. Chem. 108 (1996), 1312–13 or EP 278 384). In this process, the unsaturated 2-cyclododecylpropionic ester is formed in a Reformatsky reaction with zinc. Zinc bromide is produced and has to be disposed of. The resulting ester is subsequently catalytically hydrogenated or, as disclosed in EP 278 384, reduced with lithium aluminum hydride. Compounds formed via organohalogen compounds generally still contain traces of halogen. Since hydrogen halide is formed therefrom on hydrogenation, severe corrosion of the reactor material and of the hydrogenation catalyst is to be expected on catalytic hydrogenation of the ester to the corresponding alcohol. Moreover, it is known that traces of halogen of as little as about 1 ppm interfere.

The process described above is very suitable for preparing small amounts of 2-cyclododecyl-1-propanol. However, this process is unsuitable for industrial preparation, i.e. for preparing 2-cyclododecyl-propanol [sic] on the scale of tonnes, for the following reasons:

1. The alkyl 2-bromopropionates used as starting compounds, and thus the alkyl alpha-bromo-zincpropionates [sic] obtainable therefrom, are rather costly.
2. The preparation of the cyclododecanone by hydrogenation of cyclododecatriene and subsequent oxidation of the resulting cyclododecane is rather complicated industrially and therefore also costly.
3. The formation of hydrogen halides, which has been described above, on hydrogenation leads to corrosion problems for the reactors and the hydrogenation catalysts, which entails the need to use extremely costly reactor materials and leads to short service lives of the hydrogenation catalysts.
4. The zinc bromide produced in the reaction leads to great waste-water problems and requires complicated workup or disposal measures.
5. The reduction with lithium aluminum hydride described in EP 278 384 is prohibitive for industrial synthesis.

It is an object of the present invention to develop a process for industrial preparation of 2-cyclododecyl-propanol [sic] which avoids the disadvantages of the prior art process. The novel process ought thus to start from materials which are as easily obtainable and therefore as cheap as possible and ought to result, in the minimum number of reaction steps which are easy to carry out industrially, and in good yields, in an olfactorily pleasing product without causing waste-water problems due to high salt production.

We have found that this object is achieved by preparing 2-cyclododecyl-1-propanol even on the industrial scale by reacting cyclododecene with an excess of propionic acid or a propionic acid derivative in the presence of catalytic amounts of a free-radical initiator, and hydrogenating the 2-cyclododecyl-propionic acid which is formed, or the corresponding 2-cyclododecylpropionic acid derivatives, catalytically with hydrogen on hydrogenation catalysts.

It was surprising that hydroxyambrane, which is in demand, can be prepared in an olfactorily satisfactory purity in this way in a synthesis which can easily be carried out industrially and comprises only two reaction stages starting from cyclododecene, which can easily be prepared by trimerization of butadiene and subsequent partial hydrogenation.

Although Synthesis (1970) No. 3, 99 –140, had disclosed that addition of carboxylic acids or carboxylic acid derivatives onto olefins is possible in the presence of free-radical initiators, the yields obtained according to loc.cit. on reaction of the cycloolefins cyclopentene and cyclohexene are only 17 and 10%, respectively, of theory, in contrast to good yields on reaction of numerous open-chain olefins, so that it was absolutely impossible to expect that it would be possible to obtain yields satisfactory for industrial preparation on reaction with cyclododecene.

Methoden der organischen Chemie (Houben-Weyl), Volume V/1b, 4th edition 1997, pages 1058–1063, has also disclosed the free-radical addition of carboxylic acids or carboxylic acid derivatives onto olefins. However, addition of propionic acid or its derivatives onto cyclododecene as olefin was not mentioned anywhere. Since relatively large amounts of unwanted byproducts are generally formed in reactions initiated by free-radical initiators, it was additionally not to be expected that hydroxyambrane can be prepared in olfactorily adequate purity by such a reaction.

The invention accordingly relates to a process for preparing 2-cyclododecyl-propanol [sic] which comprises A. reacting cyclododecene with propionic acid or one of its derivatives in the presence of catalytic amounts of a free-radical initiator and B. reacting the 2-cyclododecylpropionic acid which is formed, or the corresponding derivative, with hydrogen on suitable hydrogenation catalysts at from 100 to 300° C. and under from 20 to 350 bar.

The novel process is particularly advantageous when propionic acid derivatives used are its esters with lower ($C_1$–$C_6$) alkanols.

The novel process is particularly advantageous when the free-radical initiators are hydrogen peroxide, perborates, perdisulfates, permonosulfates, peracids, hydroperoxides, dialkyl peroxides, peresters, diacyl peroxides, peroxydicarbonates, perketals or ketone peroxides, in particular di-tert-butyl peroxide which is readily available.

The second reaction step, the catalytic hydrogenation, takes place well when the hydrogenation catalyst used contains one or more elements of groups Ib, VIb, VIIb and VIIIb, and IIIa, IVa and Va, of the Periodic Table of the Elements, especially when the hydrogenation catalyst used contains at least one of the elements copper, cobalt or rhenium.

The cyclododecene used as starting compound can easily be prepared by trimerization of butadiene to cyclododecatriene (cf. Angew. Chem. 75 (1963) 10) and subsequent partial hydrogenation thereof. Complete hydrogenation and subsequent oxidation of the resulting cyclododecane to cyclododecanone as in the known preparation process is therefore unnecessary.

The free radicals necessary for addition of the carboxylic acid or its derivatives can be generated by generally known methods. Examples which may be mentioned are irradiation and decompositon of free-radical initiators such as peroxides. Decomposition of peroxides is preferred. Examples of peroxides which may be mentioned are hydrogen peroxide, perborates, perdisulfates, permonosulfates, peracids, hydroperoxides, dialkyl peroxides, peresters, diacyl peroxides, peroxydicarbonates, perketals and ketone peroxides. Decomposition of the free-radical initiators is advantageously induced thermally. The peroxy compounds are employed in catalytic amounts. Thus, in general, from 0.01 to 1, preferably 0.05 to 0.8, in particular 0.1 to 0.6, mole equivalents of peroxy compound are used according to the invention per mole of cyclic olefin. The temperature for the free-radical addition depends on the peroxy compound employed. Since each peroxy compound starts to decompose at a different temperature, the temperature range for the novel process is quite large. It is generally from 30 to 250° C. If, for example, di-tert-butyl peroxide is employed, the temperature is preferably 120–160° C.

The reaction is generally carried out under a pressure at which the reactants are in the liquid state, there being no upper limit on the pressure.

The molar ratio of propionic acid or its derivatives to cyclododecene is generally between 400 and 1, preferably between 150 and 1 and, in particular, between 100 and 1. The propionic acid or its derivative moreover advantageously serves as solvent.

Particularly suitable propionic acid derivatives for the novel reaction are its esters. Particularly suitable esters which may be mentioned are the methyl, ethyl, propyl, n-butyl, isobutyl, tert-butyl, tert-amyl, n-pentyl and n-hexyl esters. However, amides or propionic anhydride can also be employed.

The reaction can be carried out batchwise, semicontinuously or continuously.

The discharge from the reaction can be worked up before the second process step, the hydrogenation, but can also be employed directly in the next stage. Workup is generally confined to removing the excess propionic acid or the excess propionic acid derivative and unreacted cyclic olefin. Said low-boilers are preferably removed by distillation. They can be returned to the first stage of the process.

If it is wished to obtain pure 2-cyclododecylpropionic acid, the residue after removal of the propionic acid can itself be distilled, or the acid can be obtained in pure form by crystallization. Hydrogenation of 2-cyclododecylpropionic acid or hydrogenation of its derivatives can be carried out using the crude discharge from the first stage of the process, the crude discharge after removal of propionic acid or propionic acid derivatives, or the pure substances, in the gas or liquid phase.

The hydrogenation catalysts generally used in the novel process are heterogeneous catalysts, but it is also possible to use homogeneous catalysts which are suitable for hydrogenating carbonyl groups. They can either be arranged as fixed bed catalysts or be employed in mobile form, for example in a fluidized bed reactor. Examples of hydrogenation catalysts for this purpose are described, for example, in Houben-Weyl, Methoden der organischen Chemie, Volume IV/1c, pages 16 to 26.

Preferred hydrogenation catalysts among these are those comprising one or more elements of group Ib, VIb, VIIb and VIII, and IIIa, IVa and Va, of the Periodic Table of the Elements, in particular copper, chromium, rhenium, cobalt, rhodium, nickel, palladium, iron, platinum, indium, tin and antimony.

The catalysts employed in the novel process may be, for example, precipitated catalysts. Catalysts of this type can be prepared by precipitating their catalytically active components from solutions of salts thereof, in particular from solutions of their nitrates and/or acetates, for example by adding alkali metal and/or alkaline earth metal hydroxide and/or alkali metal and/or alkaline earth metal carbonate solutions, in the form of their sparingly soluble hydroxides, oxide hydrates, basic salts or carbonates, then drying the resulting precipitates and subsequently converting them by calcination at, in general, from 300 to 700° C., in particular 400 to 600° C., into the corresponding oxides, mixed oxides and/or mixed valency oxides, which are reduced, and thus converted into the actual catalytically active form, by treatment with hydrogen or hydrogen-containing gases at, as a rule, 50–700° C., in particular 100–400° C., to give the relevant metals and/or oxides of lower oxidation state. This reduction is, as a rule, continued until water is no longer formed. To prepare precipitated catalysts containing a carrier material, the catalytically active components can be precipitated in the presence of the relevant carrier material. However, it is also possible advantageously for the catalytically active components to be precipitated simultaneously with the carrier material from the relevant salt solutions. The hydrogenation catalysts preferably employed in the novel process are those containing the metals or metal compounds which catalyze the hydrogenation deposited on a carrier material. Suitable carrier materials for the catalysts of the novel process are, in general, those in which the components catalyzing the hydrogenation have been applied to a carrier material for example by impregnation.

The way in which the catalytically active metals are applied to the carrier is, as a rule, not critical and can be brought about in various ways. The catalytically active metals can be applied to these carrier materials for example by impregnation with solutions or suspensions of the salts or oxides of the relevant elements, drying and subsequent reduction of the metal compounds to give the relevant metals or compounds of a lower oxidation state by means of a reducing agent, preferably with hydrogen or complex hydrides. Another possibility for applying the catalytically active metals to these carriers consists of impregnating the carriers with solutions of salts which readily undergo thermal decomposition, e.g. with nitrates, or complex compounds which readily undergo thermal decomposition, e.g. carbonyl or hydrido complexes of the catalytically active metals, and heating the carrier impregnated in this way to from 300 to 600° C. for thermal decomposition of the adsorbed metal compounds. This thermal decomposition is preferably carried out under a protective gas atmosphere. Examples of suitable protective gases are nitrogen, carbon dioxide, hydrogen or the inert gases. The catalytically active metals can furthermore be deposited on the catalyst carrier by vapor deposition or by flame spraying. The content of catalytically active metals in these supported catalysts is not in principle critical for success of the novel process. It is self-evident to the skilled worker that greater contents of catalytically active metals in these supported catalysts may result in higher space-time conversions than lower contents. The supported catalysts generally used contain from 0.1 to 90% by weight, preferably 0.5 to 40% by weight, of catalytically active metals, based on the complete catalyst. Since these content data refer to the complete catalyst including carrier material, but different carrier materials have very different specific gravities and specific surface areas, data lower or higher than these are also possible without this necessarily having a disadvantageous effect on the result of the novel process. It is, of course, also possible to apply a plurality of catalytically active metals to the particular carrier material. Furthermore, the catalytically active metals can be applied to the carrier for example by the process of DE-A 2 519 817, EP-A 147 219 and EP-A 285 420. The catalytically active metals are present in the catalysts disclosed in the abovementioned publications as alloys which are produced by thermal treatment and/or reduction of the, for example, by [sic] impregnation with a salt or complex of the abovementioned metals.

Activation both of the precipitated catalysts and of the supported catalysts can also take place at the start of the reaction in situ by the hydrogen which is present, but these catalysts are preferably activated separately before being used.

Carrier materials which can in general be employed are the oxides of aluminum and titanium, zirconium dioxide, silicon dioxide, clays such as montmorillonites, silicates such as magnesium or aluminum silicates, zeolites, such as ZSM-5 or ZSM-10 zeolites, or active carbon. Preferred carrier materials are aluminum oxides, titanium dioxides, silicon dioxide, zirconium dioxide and active carbon. It is, of course, also possible to use mixtures of various carrier materials as carrier for the catalysts which can be used in the novel process.

Examples of heterogeneous catalysts which can be employed for the novel process are the following:

cobalt on active carbon, cobalt on silicon dioxide, cobalt on aluminum oxide, rhenium on active carbon, rhenium on silicon dioxide, rhenium/tin on active carbon, rhenium/platinum on active carbon, copper on active carbon, copper/silicon dioxide, copper/aluminum oxide, copper chromite, barium copper chromite, copper/aluminum oxide/manganese oxide, copper/aluminum oxide/zinc oxide, and the catalysts disclosed in DE-A 3 932 332, U.S. Pat. No. 3,449,445, EP-A 44 444, EP-A 147 219, DE-A 3 904 083, DE-A 2 321 101, EP-A 415 202, DE-A 2 366 264, EP 0 552 463 and EP-A 100 406.

Particularly preferred catalysts comprise at least one of the metals copper, cobalt or rhenium.

The novel process can advantageously be carried out continuously. It is possible to use for this, for example, tubular reactors in which the catalyst is advantageously arranged in the form of a fixed bed, or fluidized bed reactors in which the catalyst is agitated by the gas stream.

The hydrogenation can be carried out with and without solvent. If a solvent is employed, it may be water or an alcohol such as methanol or ethanol. Also suitable are ethers such as tetrahydrofuran, dioxane or ethylene glycol dimethyl ether, and hydrocarbons such as hexane or cyclohexane.

The hydrogenation is carried out at from 100 to 300° C., preferably 150 to 260° C. If the hydrogenation is carried out in the gas phase, the pressure is from 20 to 80 bar. If it is carried out in the liquid phase, the pressure is from 50 to 350 bar, preferably from 100 to 320 bar, in particular from 130 to 300 bar.

The novel process is to be illustrated in detail, but not restricted in any way, by the following example.

EXAMPLE 1

370 g (5 mol) of propionic acid were heated to 140° C. in a reaction vessel. Then a mixture of 84 g (0.5 mol) of cyclododecene and 14.6 g (0.1 mol) of di-tert-butyl peroxide was added dropwise over the course of 5 hours (h). This was followed by refluxing for a further 2 h. After the reaction mixture had been cooled, the excess propionic acid and the tert-butyl alcohol which had formed were distilled off under 30 mbar. The pressure was lowered and then unreacted cyclododecene was distilled off to leave 31 g of residue.

The residue obtained was dissolved in 280 ml of ethanol and hydrogenated batchwise with hydrogen in an autoclave at 220° C. under 220 bar for 2 h on 31 g of a copper catalyst which had the following composition in its non-activated form: 70% by mass CuO, 25% by mass ZnO and 5% by mass $Al_2O_3$, and had been activated with hydrogen at 180° C. The mixture was then cooled and decompressed. Analysis by gas chromatography (GC) showed that the discharge contained, subtracting ethanol, 57.7% 2-cyclododecyl-propanol and 14% ethyl 2-cyclododecylpropionate, the remainder being mainly high-boiling products. The yield of the required hydroxyambrane was about 60% of theory based on reacted cyclododecene with a conversion of 64%.

EXAMPLE 2

880 g (10 mol) of methyl propionate, 163 g (0.94 mol) of a 96% by weight cyclododecene and 26 g (0.18 mol) of di-tert-butyl peroxide were reacted by stirring in an autoclave at 140° C. under an autogenous pressure of 5.1 bar for 20 h.

The reaction discharge contained by GC analysis 98 g of cyclododecene and 50 g of methyl 2-cyclododecylpropionate. This corresponds to a selectivity of 52% and a conversion of 60%.

After distillation, the methyl 2-cyclododecylpropionate had a boiling point of 112° C./3 mbar.

EXAMPLE 3

500 g of a residue obtained as in Example 1 by addition reaction of propionic acid and cyclododecene were dissolved in 500 g of n-butanol und hydrogenated continuously (feed about 20 g/h, 220 bar, 220–230° C.) on 25 ml of a cobalt catalyst prepared as in Example 1 in DE 23 21 101 in a downflow process in a tubular reactor. To complete the conversion, the hydrogenation discharge was rehydrogenated under the same conditions.

The discharge contained, excepting the solvent n-butanol, about 70% 2-cyclododecyl-propanol. The other consistuents were mainly cyclododecane diners and oligomers. The hydrogenation discharge was, after removal of butanol, fractionally distilled in a 1 m high packed column under 1 mbar. With a bottom temperature of 185° C. a total of 260 g of 2-cyclododecyl-propanol with a purity of 97–99.8% were obtained at boiling points between 123 and 132° C. All the fractions obtained had an odor of satisfactory quality.

We claim:

1. A process for preparing 2-cyclododecyl-1-propanol which comprises

A. reacting cyclododecene with propionic acid or one of its derivatives in the presence of catalytic amounts of a free-radical initiator and B. reacting the 2-cyclododecylpropionic acid which is formed, or the corresponding derivative, with hydrogen on suitable hydrogenation catalysts at from 100 to 300° C. and under pressure from 20 to 350 bar.

2. A process as claimed in claim 1, wherein the propionic acid derivatives used are its esters with lower alkanols.

3. A process as claimed in claim 1, wherein the free-radical initiators used are hydrogen peroxide, perborates, perdisulfates, permonosulfates, peracids, hydroperoxides, dialkyl peroxides, peresters, diacyl peroxides, peroxydicarbonates, perketals or ketone peroxides.

4. A process as claimed in claim 3, wherein di-tert-butyl peroxide is used as free-radical initiator.

5. A process as claimed in claim 1, wherein the hydrogenation catalyst used comprises one or more elements of groups Ib, VIb, VIIb and VIIIb, and IIIa, IVa and Va, of the Periodic Table of the Elements.

6. A process as claimed in claim 1, wherein the hydrogenation catalyst used comprises at least one of the elements copper, cobalt or rhenium.

7. A process as claimed in claim 1, wherein propionic anhydride is used as propionic acid derivative.

* * * * *